United States Patent [19]

Baasner et al.

[11] Patent Number: 4,703,121

[45] Date of Patent: Oct. 27, 1987

[54] PROCESS FOR THE PREPARATION OF 5-FLUOROCYTOSINE

[75] Inventors: Bernd Baasner, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 790,585

[22] Filed: Oct. 23, 1985

[30] Foreign Application Priority Data

Nov. 14, 1984 [DE] Fed. Rep. of Germany ....... 3441524

[51] Int. Cl.[4] ........................................... C07D 239/30
[52] U.S. Cl. ................................................... 544/317
[58] Field of Search ......................................... 544/317

[56] References Cited

U.S. PATENT DOCUMENTS

| | | | |
|---|---|---|---|
| 2,945,038 | 7/1960 | Duschinsky et al. | 544/317 |
| 3,846,429 | 11/1974 | Giller et al. | 544/313 |
| 3,954,758 | 5/1976 | Schuman et al. | 544/303 |
| 4,113,949 | 9/1978 | Schuman et al. | 544/303 |
| 4,473,691 | 9/1984 | Takahara | 544/317 |

FOREIGN PATENT DOCUMENTS 877318 9/1961 United Kingdom .

OTHER PUBLICATIONS

Robert Filler and S. M. Naqvi in "Biomedical Aspects of Fluorine Chemistry", Eds. R. Filler and Y. Kobayashi, Elsevier, Amsterdam-New York-Oxford (1982).
J. Am. Chem. Soc., 79; 4559 (1957).
Kjell Undheim and Michel Gacek in "Some Derivatives of 5-Fluoropyrimidine", Chemical Institute University of Oslo, Acta Chem. Scand., 23, 294 (1969).

*Primary Examiner*—Donald G. Daus
*Assistant Examiner*—Cecilia Shen
*Attorney, Agent, or Firm*—Sprung Horn Kramer & Woods

[57] ABSTRACT

5-fluorocytosine is prepared by reacting 2,5-difluoro-4-chloro-pyrimidine with a proton acid in the presence of water to yield 2-hydroxy-4-chloro-5-fluoropyrimidine and reacting the 2-hydroxy-4-chloro-5-fluoropyrimidine with ammonia to yield 5-fluoro-cytosine.

15 Claims, No Drawings

PROCESS FOR THE PREPARATION OF 5-FLUOROCYTOSINE

BACKGROUND OF THE INVENTION

The present invention relates to a new process for the preparation of 5-fluorocytosine, which can also be called 2-hydroxy-4-amino-5-fluoropyrimidine.

5-Fluorocytosine is known as a pharmaceutical and as an intermediate for the preparation of pharmacologically active substances (see, for example, R. Filler and S. M. Naqvi in "Biomedicinal Aspects of Fluorine Chemistry", Eds. R. Filler and Y. Kobayashi, Elsevier, Amsterdam-New York-Oxford, 1982). It was hitherto prepared by direct fluorination of cytosine (see U.S. Pat. No. 3,846,429 and Canadian Patent Specification No. 985,681), which required industrially expensive handling of elemental fluorine, or by expensive cyclization reactions of α-fluoro-β-keto-ester enolates with salts of isothioureas (see J. Am. Chem. Soc. 79, 4559 (1957)).

Another synthesis starts from 5-fluorouracil, a compound which can also be prepared only in an expensive manner by direct fluorination of the uracil with elemental fluorine (see U.S. Pat. No. 3,846,429 and Canadian Patent Specification No. 985,681), or by expensive cyclization reactions (see J. Am. Chem. Soc. 79, 4559 (1957)). The 5-fluorouracil must then also be further converted into 2,4-dichloro-5-fluoropyrimidine with phosphorus oxychloride. The amino group is subsequently introduced into the 4-position and the hydroxyl group is then introduced into the 2-position and, finally, 2-hydroxy-4-amino-5-fluoropyrimidine (≙5-fluorocytosine) is thus obtained (see British Patent Specification 877,318). This route comprises many individual stages and is therefore very difficult, and uses 5-fluorouracil, which is accessible only with difficulty, as the starting substance.

It is also known that 2-hydroxy-4-chloro-5-fluoropyrimidine—this compound is encountered as an intermediate in the process according to the invention—can be synthesized by a process in which 5-fluorouracil is again used as the starting substance and is sulphurized in the 4-position with P₂S₅, and the compound then obtained, that is to say 5-fluoropyrimidine-2-one-4-thione, is subsequently converted into 2-hydroxy-4-chloro-5-fluoropyrimidine with thionyl chloride (see Acta Chem. Scand. 23, 294 (1969)). This process has the disadvantage that more expensive reagents than in the process according to the invention are employed and more expensive working up and disposal measures must be taken. In addition, the yield in the last stage is only 45% of theory.

SUMMARY OF THE INVENTION

A process has now been found for the preparation of 5-fluorocytosine, which is characterised in that 2,5-difluoro-4-chloropyrimidine is reacted with a proton acid in the presence of water to give 2-hydroxy-4-chloro-5-fluoropyrimidine, and this is reacted with ammonia to give 2-hydroxy-4-amino-5-fluoropyrimidine (≙5-fluorocytosine).

DETAILED DESCRIPTION OF THE INVENTION

The process according to the invention can be illustrated by the following equation:

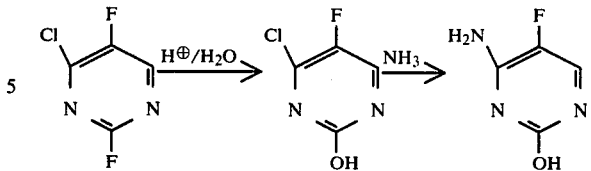

According to the invention, 2,5-difluoro-4-chloropyrimidine is reacted with a proton acid in the presence of water in a first stage. The proton acid employed can be of any desired nature and strength. Strong proton acids in the form of aqueous solutions of any desired concentration are preferably employed. Dilute and concentrated aqueous solutions of hydrochloric acid, sulphuric acid and phosphoric acid are particularly preferred.

The proton acid and the water should in general be added in an amount such that at least one mole of protons and at least one mole of water are available per mole of 2,5-difluoro-4-chloropyrimidine. Excesses of proton acid and/or water, even relatively large excesses, present no problems. For economic reasons, it is preferable to employ 1 to 2 moles of proton acid and 2 to 100 moles of water per mole of 2,5-difluoro-4-chloropyrimidine.

Suitable reaction temperatures for this reaction stage are, for example, those in the range from 0° to 150° C. Temperatures in the range from 0° to 100° C. are preferred.

2-Hydroxy-4-chloro-5-fluoropyrimidine is obtained in this manner, in general in yields of more than 90% of theory. If appropriate, this compound can be isolated by customary methods, for example by first removing all the volatile constituents of the reaction mixture under normal pressure or in vacuo, taking up the residue in water, rendering this mixture neutral and then precipitating the 2-hydroxy-4-chloro-5-fluoropyrimidine by concentrating the solution and separating it off. For the neutralization, a pH value of at least 7, preferably a pH value of 7 to 8, is established, for example by addition of an aqueous solution of ammonia, an alkali metal carbonate or an alkali metal bicarbonate.

According to the invention, the 2-hydroxy-4-chloro-5-fluoropyrimidine is reacted with ammonia in a second stage, the chlorine bonded in the 4-position being replaced by an amino group. The amount of ammonia can be varied within wide limits. For example, 1 to 20 moles of ammonia can be employed per mole of 2-hydroxy-4-chloro-5-fluoropyrimidine. The use of 1 to 8 moles of ammonia per mole of 2-hydroxy-4-chloro-5-fluoropyrimidine is preferred.

The reaction with ammonia can be carried out in the most diverse ways. For example, the ammonia can be employed in condensed form by bringing it together with 2-hydroxy-4-chloro-5-fluoropyrimidine at temperatures below its boiling point. Preferably, in this case, 2-hydroxy-4-chloro-5-fluoropyrimidine is added in small portions, if appropriate in dissolved form, to the condensed ammonia. The reaction mixture can then be warmed, for example to room temperature or higher temperatures, but the reaction has as a rule already ended when the temperature reaches +10° C.

The ammonia can also be employed in the form of solutions of any desired concentration, solutions in organic solvents, such as tetrahydrofuran, diethyl ether or dioxane, and solutions in water being preferred. In this case, the ammonia solution can be taken and the 2-hydroxy-4-chloro-5-fluoropyrimidine, if appropriate dissolved in a solvent, such as tetrahydrofuran, diethyl ether, dioxane, methanol or ethanol, can be added, or the reverse procedure can be followed.

If the ammonia is employed in the form of aqueous solutions, concentrated solutions are preferred, for example those containing 20 to 33% by weight of ammonia. In this case, it is furthermore advantageous to carry out the reaction in the presence of a water-miscible solvent, for example in the presence of methanol, ethanol, dioxane and/or tetrahydrofuran.

The temperature for the reaction with ammonia can be, for example, in the range from $-80°$ to $+60°$ C. Temperatures in the range from $-40°$ to $+30°$ C. are preferred.

The reaction with ammonia is particularly preferably carried out by adding a concentrated aqueous solution of ammonia to a solution of 2-hydroxy-4-chloro-5-fluoropyrimidine in methanol, ethanol, dioxane and/or tetrahydrofuran.

The reaction with ammonia is in general ended after 1 to 8 hours. The 2-hydroxy-4-amino-5-fluoropyrimidine ($\hat{=}$5-fluorocytosine) thereby obtained in most cases precipitates out of the reaction mixture in crystalline form during the reaction, or if appropriate only after concentration of the reaction mixture, and can be obtained therefrom in a simple manner by filtration and drying. A procedure can also be followed in which the volatile constituents are first removed, by distillation in vacuo, from the mixture present after the reaction with ammonia, the residue is taken up in a little water and the product, which largely remains undissolved, is filtered off and dried. The purity of the resulting product is in this case usually more than 98.5%, without recrystallisation being carried out.

To carry out the second stage of the process according to the invention, it is not necessary to isolate the 2-hydroxy-4-chloro-5-fluoropyrimidine after the first stage. It is also possible to add to the entire mixture present after the first reaction stage ammonia in an amount which is at least necessary for neutralization of the mixture and for the conversion of the 2-hydroxy-4-chloro-5-fluoropyrimidine present into 2-hydroxy-4-amino-5-fluoropyrimidine. In this case, the ammonia is preferably used in the form of a concentrated aqueous solution and the reaction is carried out in the presence of a water-miscible solvent, such as methanol, ethanol, tetrahydrofuran and/or dioxane. After the working up described above, products with purities of more than 98.5% are also usually obtained.

Independently of whether the 2-hydroxy-4-chloro-5-fluoropyrimidine is isolated or not after the first stage, 2-hydroxy-4-amino-5-fluoropyrimidine (=fluorocytosine) is in general obtained in yields of 88 to 93% of theory (calculated over both stages) by the two-stage process according to the invention.

The process according to the invention and the advantages which can thereby be achieved are decidedly surprising, since according to British Patent Specification No. 877,318 it was to be expected that the first nucleophilic reaction of the 2,5-difluoro-4-chloropyrimidine, if not exclusively then at least quite predominantly, takes place in the 4-position, and 2,5-difluoro-4-hydroxy-pyrimidine was thus to be expected as a product of the first stage.

The 2,5-difluoro-4-chloropyrimidine required as the starting substance for carrying out the process according to the invention is accessible in a simple manner by partial selective hydrogenation of 2,5-difluoro-4,6-dichloropyrimidine in accordance with an earlier patent application which has been filed by the assignee (see the following Example 1).

The following examples illustrate the process according to the invention without limiting it in any way.

EXAMPLES

EXAMPLE 1

(not according to the invention)

Preparation of 2,5-difluoro-4-chloropyrimidine from 2,5-difluoro-4,6-dichloropyrimidine 185 g (1 mole) of 2,5-difluoro-4,6-dichloropyrimidine were hydrogenated in 1,800 ml of ethyl acetate, with the addition of 110 g of triethylamine and 15 g of palladium-on-charcoal (5% strength by weight), at 30° C. under a hydrogen pressure of 3.5 bar in a stainless steel stirred autoclave for 95 minutes. The solid contents of the reaction mixture were then filtered off, the residue was washed with ethyl acetate and the filtrate was combined with the wash liquid and distilled under normal pressure over a 30 cm packed column. When the solvent had distilled off, 106 g of 2,5-difluoro-4-chloropyrimidine with a boiling point of 145° to 146° C. were obtained. The yield was accordingly 70.5% of theory. After analysis by gas chromatography, the isolated reaction product had a purity of 94.7%.

The 2,5-difluoro-4,6-dichloropyrimidine required for this preparation of 2,5-difluoro-4-chloropyrimidine is likewise accessible in accordance with an earlier patent application which has been filed by the assignee (application Ser. No. 693,077, filed Jan. 22, 1985) for, example, by reacting tetrafluoropyrimidine, which is known, with hydrogen chloride gas under increased pressure at elevated temperature (for example 30 bar of hydrogen chloride and 160° C.) and subjecting the mixture thereby obtained to fractional distillation.

EXAMPLE 2

Preparation of 2-hydroxy-4-chloro-5-fluoropyrimidine 15.05 g (0.1 mole) of 2,5-difluoro-4-chloropyrimidine were heated under reflux together with 30 ml of 37% strength aqueous hydrochloric acid for 2 hours. The volatile constituents were then stripped off in vacuo, the residue was taken up in 100 ml of water and this mixture was rendered weakly alkaline (pH 7.5) with 20% strength aqueous ammonia. The mixture was then again concentrated in vacuo down to 20% of the original volume. The solid obtained was filtered off with suction and dried. 13.7 g of product with a melting point of 176° to 177° C. (decomposition) were obtained, corresponding to a yield of 92.2%.

EXAMPLE 3

Preparation of 5-fluorocytosine from 2-hydroxy-4-chloro-5-fluoropyrimidine 14.85 g (0.1 mole) of 2-hydroxy-4-chloro-5-fluoropyrimidine, which was obtained according to Example 2, were suspended in 100 ml of ethanol. 20 ml of 33% strength aqueous ammonia solution were added dropwise at room temperature, with stirring, and the mixture was subsequently stirred for 90 minutes. It was then concentrated in vacuo to one third of the original volume and the solid obtained was filtered off with suction, washed with water and dried. 12.64 g of product with a melting point of 294° to 295° C. were obtained, corresponding to a yield of 98% of theory.

EXAMPLE 4

Preparation of 5-fluorocytosine from 2,5-difluoro-4-chloropyrimidine 15.05 g (0.1 mole) of 2,5-difluoro-4-chloropyrimidine were stirred in 30 ml of 37% strength aqueous hydrochloric acid at 50° C. for 2 hours. After the mixture had cooled, it was neutralized with 33% strength aqueous ammonia solution. The mixture was then diluted with 100 ml of ethanol and a further 20 ml of aqueous 33% strength ammonia solution were added. The mixture was subsequently stirred at room temperature for 2 hours. Thereafter, it was concentrated in vacuo, the residue was taken up in 60 ml of water and the solid obtained was filtered off with suction, washed with water and dried. 11.5 g of product with a melting point of 294° to 296° C. were obtained, corresponding to a yield of 98.1% of theory.

It will be understood that the specification and examples are illustrative but not limitative of the present invention and that other embodiments within the spirit and scope of the invention will suggest themselves to those skilled in the art.

What is claimed:

1. A process for the preparation of 5-fluorocytosine comprising reacting 2,5-difluoro-4-chloropyrimidine with a proton acid in the presence of water to yield 2-hydroxy-4-chloro-5-fluoropyrimidine, and reacting the 2-hydroxy-4-chloro-5-fluoropyrimidine with ammonia to yield 5-fluorocytosine.

2. A process according to claim 1, wherein the proton acid is a strong proton acid.

3. A process according to claim 1, wherein the proton acid is an aqueous solution of hydrochloric acid, sulphuric acid or phosphoric acid.

4. A process according to claim 1, wherein 1 to 2 moles of the proton acid and 2 to 100 moles of water are employed per mole of 2,5-difluoro-4-chloro-pyrimidine.

5. A process according to claim 1, wherein the reaction of the proton acid and the 2,5-difluoro-4-chloropyrimidine is carried out at temperatures in the range from 0° C. to 150° C.

6. A process according to claim 1, wherein the reaction of the proton acid and the 2,5-difluoro-4-chloropyrimidine is carried out at temperatures in the range from 0° C. to 100° C.

7. A process according to claim 1, wherein 1 to 20 moles of ammonia are employed per mole of 2-hydroxy-4-chloro-5-fluoropyrimidine.

8. A process according to claim 1, wherein 1 to 8 moles of ammonia are employed per mole of 2-hydroxy-4-chloro-5-fluoropyrimidine.

9. A process according to claim 1, wherein the reaction of the 2-hydroxy-4-chloro-5-fluoropyrimidine with ammonia is carried out at temperatures in the range from −80° C. to +60° C.

10. A process according to claim 1, wherein the reaction of the 2-hydroxy-4-chloro-5-fluoropyrimidine with ammonia is carried out at temperatures in the range from −40° C. to +30° C.

11. A process according to claim 1, wherein the ammonia is employed as a 20 to 33% strength by weight aqueous ammonia solution and the reaction of ammonia and the 2-hydroxy-4-chloro-5-fluoropyrimidine is carried out in the presence of a water-miscible solvent.

12. A process according to claim 1, wherein the 2-hydroxy-4-chloro-fluoropyrimidine is not isolated, but ammonia is added to the entire mixture present after the reaction of 2,5-difluoro-4-chloropyrimidine with a proton acid.

13. A process according to claim 12, wherein 20 to 33% strength by weight aqueous ammonia is employed and the reaction is carried out in the presence of a water-miscible solvent.

14. A process according to claim 13, wherein the water-miscible solvent is selected from the group consisting of methanol, ethanol, dioxane, tetrahydrofuran and mixtures thereof.

15. A process according to claim 1, wherein the reaction of ammonia and the 2-hydroxy-4-chloro-5-fluoropyrimidine is conducted for 1 to 8 hours.

* * * * *